United States Patent [19]

Ojima et al.

[11] Patent Number: 5,147,361

[45] Date of Patent: Sep. 15, 1992

[54] VERTEBRAL CONNECTING PLATE

[75] Inventors: Satoshi Ojima; Hiromi Matsuzaki, both of Tokyo, Japan

[73] Assignee: Asahi Kogaku Kogyo Kabushiki Kaisha, Tokyo, Japan

[21] Appl. No.: 619,492

[22] Filed: Nov. 29, 1990

[30] Foreign Application Priority Data

Nov. 29, 1989 [JP] Japan .............................. 1-138193[U]

[51] Int. Cl.$^5$ ........................ A61B 17/56; A61B 17/58
[52] U.S. Cl. ...................................... 606/61; 606/69; 606/70; 623/17
[58] Field of Search ....................... 623/17, 18, 22, 23; 606/61, 60, 69-73

[56] References Cited

U.S. PATENT DOCUMENTS 3,741,205 6/1973 Markoff et al. ......................... 606/61
3,987,499 10/1976 Scharbach et al. .................... 623/18
4,175,555 11/1979 Herbert .................................. 606/73
4,456,005 6/1984 Lichty ............................... 606/73 X
4,655,199 4/1987 Steffee .............................. 606/61 X

FOREIGN PATENT DOCUMENTS 742618 3/1933 France ................................... 606/69

OTHER PUBLICATIONS

The Plastic and Disaster Surgery, vol. 30, 10th issue, pp. 1165-1174. (Japanese Language), 1987.

Primary Examiner—Ronald Frinks
Attorney, Agent, or Firm—Sandler, Greenblum & Bernstein

[57] ABSTRACT

A vertebral connecting plate assembly includes a vertebral connecting plate which is provided, on its opposite ends, with vertebra connecting portions to be connected to associated vertebral members or bodies. The vertebra connecting portions have threaded holes, and the set screws of the present invention have engaging screw portion, which are engaged in the associated threaded holes of the vertebral connecting plate. Thrusting screw portions of the set screws, which are thrust in the vertebral members or bodies, have a pitch (P1) larger than the pitch (P2) of the engaging screw portions.

22 Claims, 4 Drawing Sheets

VERTEBRAL CONNECTING PLATE

BACKGROUND OF THE INVENTION

1. Field of the Invention

The present invention relates to a vertebral connecting plate which is used to connect upper and lower vertebrae members. It also relates to a vertebral connecting plate assembly including the combination of a vertebral connecting plate and set screws for connecting the vertebral connecting plate to the associated vertebral members of bodies.

2. Description of the Related Art

For example, if one of the thoracic vertebrae-lumbar vertebrae is injured, the injured vertebra is removed and a transplanted bone or an artificial bone is implanted. In the surgical operation, a vertebral connecting instrument is used to mechanically connect the upper and lower vertebra members. The necessary requirements of such a vertebral connecting instrument are: ① the thickness is small, ② no loosening of the screws which are used to connect the connecting instrument and the vertebrae takes place, ③ the connecting instrument comes into close contact with the vertebrae, and ④ the connecting instrument can be implanted by an easy surgical operation, etc.

However, there is no vertebral connecting instrument which satisfies all of these requirements. Particularly, a known vertebral connecting instrument requires a highly skilled surgeon. Increased operation time causes the surgeon and the patient to become fatigued and burdened with the surgical operation.

SUMMARY OF THE INVENTION

The primary object of the present invention is to provide a vertebral connecting plate which can easily connect the upper and lower vertebrae members.

Another object of the present invention is to provide a vertebral connecting plate which has a strong connecting (fusion) force and torsion resistance.

To achieve the objects mentioned above, according to the present invention, there is provided a vertebral connecting plate assembly comprising a vertebral connecting plate which on its opposite ends provides vertebra connecting portions that connect to associated vertebral members of bodies. The vertebra connecting portions have threaded holes. The set screws of the vertebrae connecting plate assembly, have engaging screw portions which are engaged in the associated threaded holes of the vertebral connecting plate and thrusting screw portions which are thrusted in the vertebral bodies. The thrusting screw portions have a thread pitch (P1) larger than that (P2) of the engaging screw portions. Furthermore, the engaging screw portions of the set screws have a fine thread pitch and the thrusting screw portions of the set screws can have a trapezoidal thread (FIG. 2D) or a rectangular thread (FIG. 2E).

With this arrangement, due to a difference in pitch and shape of thread between the engaging screw portion and the thrusting screw portion, a further rotation of the set screw when the thrusting screw portion and the engaging screw portion are thrust into the associated vertebral body and engaged in the associated threaded hole of the vertebra connecting portion respectively, causes the thrusting screw portion to be advanced by a displacement larger than that of the engaging screw portion. This results in a rigid connection of the vertebral connecting plate to the vertebral body. The vertebra connecting plate has a strong resistance to a torsional deformation.

The present invention is also directed to a vertebral connecting plate which comprises vertebra connecting portions to be connected to associated vertebral members or bodies, and an intermediate connecting portion which connects the vertebra connecting portions. The vertebra connecting portions have threaded holes in which the associated set screws are to be screwed into.

BRIEF DESCRIPTION OF THE DRAWINGS

The invention will be described below in detail with reference to the accompanying drawings, in which.

Figures 1A, 1B, 1D:
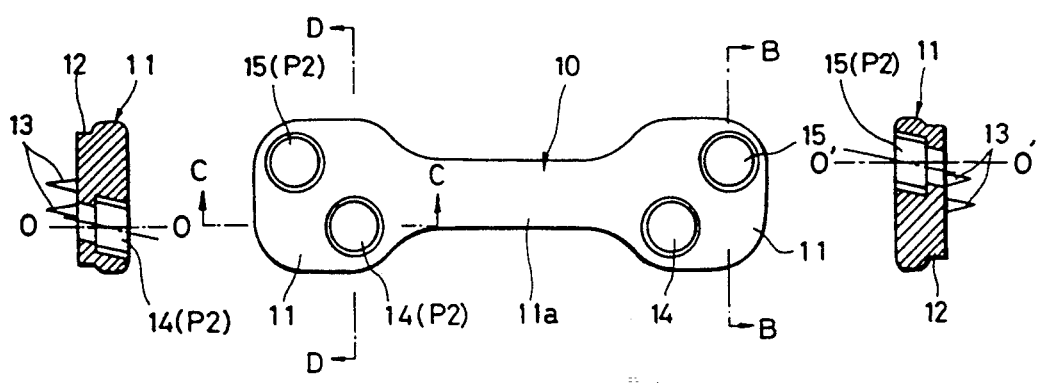
FIG. 1A is a plan view of a vertebral connecting plate according to the present invention.
FIG. 1B is a sectional view taken along the line B—B in FIG. 1A.
Figure 1C:
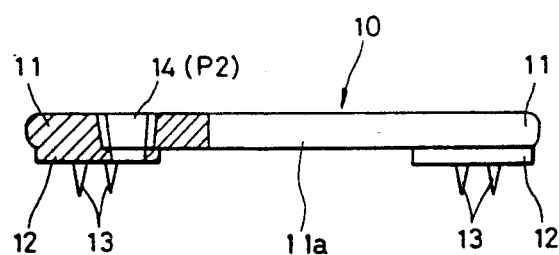
Figure 2C:
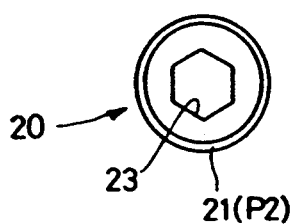
Figure 2D:
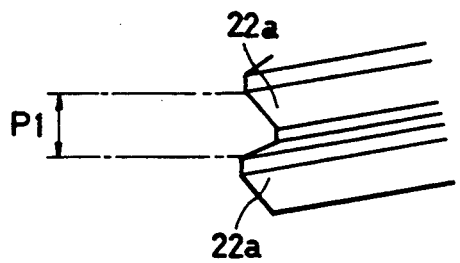
Figure 2A:
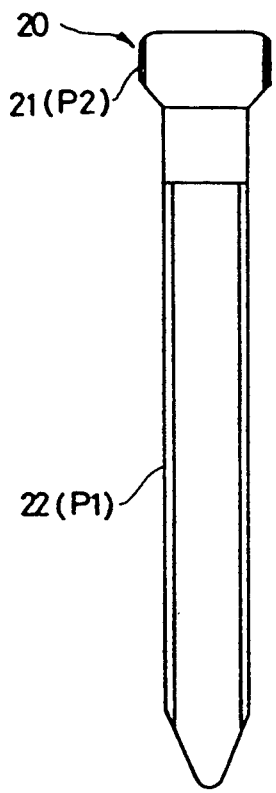
Figure 2B:
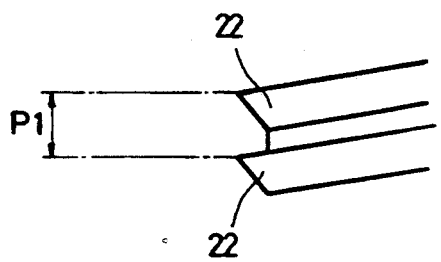
Figure 2E:
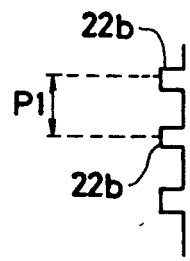
Figure 3:
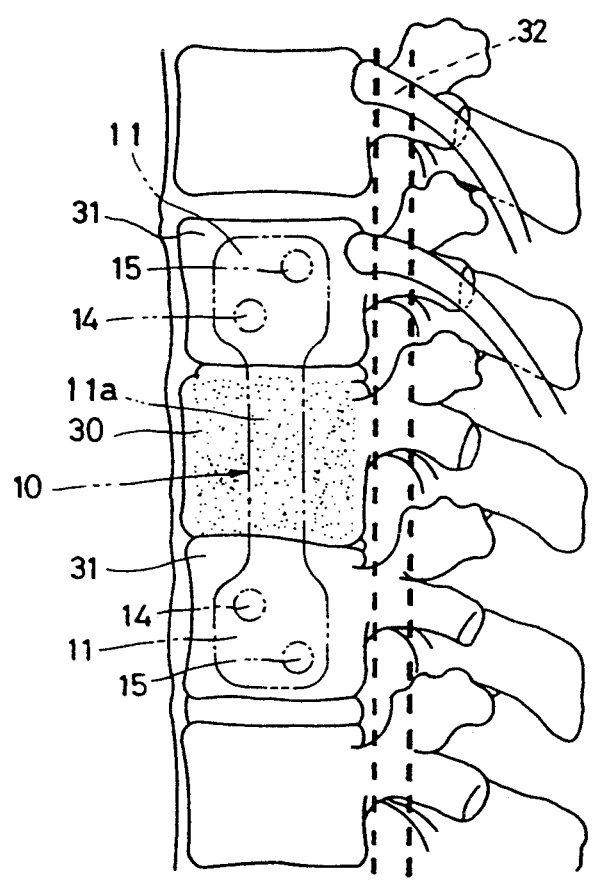
Figure 4:
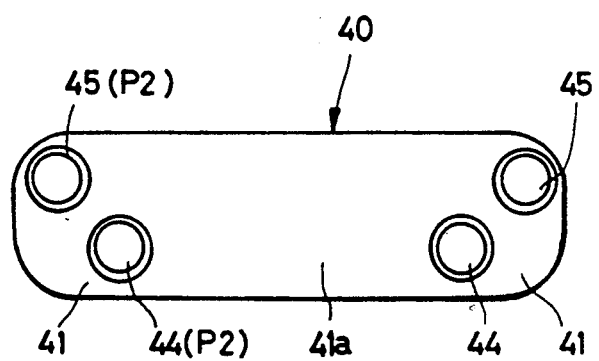

FIG, 1C is a sectional front elevation view taken along the line C—C in FIG. 1A;

FIG. 1D is a sectional view taken along the line D—D in FIG. 1A;

FIG. 2A is a plan view of a set screw used in the present invention;

FIG. 2B is an enlarged view of a thrusting thread portion of a set screw shown in FIG. 2A;

FIG. 2C is a top view of FIG. 2A;

FIG. 2D is another enlarged view of a thrusting thread portion having a trapezoidal thread of a set screw shown in FIG. 2A;

FIG. 2E is another enlarged view of a thrusting thread portion having a rectangular thread of a set screw shown in FIG. 2A;

FIG. 3 is a front elevation view of a vertebral connecting plate in use, according to the present invention; and, FIG. 4 is another embodied plan view of a vertebral connecting plate according to the present invention.

DESCRIPTION OF THE PREFERRED EMBODIMENTS

A vertebral connecting plate of the present invention, which is generally designated at 10, is made of a substantially symmetrical flat plate with respect to the center line thereof. The opposite ends of the connecting plate 10 provide vertebra connecting portions 11, which are of generally rectangular with archwise rounded corners, which are connected to each other through an intermediate narrow connecting portion 11a which has a width smaller than that of the vertebra connecting portions 11. The vertebra connecting portions 11 are provided on their rear surfaces with thickened portions 12 integral therewith which have connecting projections or sharp apexes 13 with sharp ends.

Each of the vertebra connecting portions 11 has a pair of threaded holes 14 and 15 which are substantially diagonally spaced from and opposed to each other. The threaded holes 14 and 15 are inclined inwardly with respect to axes O—O and O'—O' extending in a direction perpendicular to the plane of the vertebral connecting plate 10, as shown in FIGS. 1B and 1D, respectively. In the illustrated embodiment, the inclination angle is approximately 10 degrees. The pitch of the thread (lead of screw) of the threaded holes 14 and 15, denoted P2 is for example 1.5 mm.

Set screws 20 which are screwed in the associated threaded holes 14 and 15 have threaded heads 21 and thrusting threaded portions 22 which have a diameter smaller than that of the threaded heads 21. The threaded heads 21 preferably have a fine pitch of the thread. The threaded heads 21 have a pitch P2 (e.g., 1.5 mm) the same as that of the threaded holes 14 and 15, so that the threaded heads 21 can be screwed in the associated threaded holes 14 and 15. On the other hand, the pitch of the thread of the thrusting threaded portions 22 denoted P1 is larger than P2 (P1>P2). For example, P1 is 1.75 mm in the illustrated embodiment. As can be seen in FIG. 2B, the thrusting threaded portions 22 are made of strong screws for medical instruments and are shaped to have a strong drawing resistance.

Further, as can be seen in FIG. 2D, the thrusting threaded portions have a trapezoidal thread 22a.

As can be also seen in FIG. 2E, the thrusting threaded portions have a rectangular thread 22b. Each of the threaded heads 21 has a hexagonal open recess 23 in which a hexagonal wrench is fitted, as shown in FIG. 2C.

The vertebral connecting plate 10 and the set screw 20 are for example made of titanium alloy. As further example, the vertebral connecting plate 10 and the set screw 20 are made of titanium and stainless steel. If necessary, it is possible to coat the surfaces of the vertebral connecting plate 10 and the set screw 20 with biocompatible material, such as alumina or zirconia.

The vertebral connecting plate is used as shown in FIG. 3.

In FIG. 3, after an injured vertebral portion is removed, an artificial bone (or transplanting bone) 30 is inserted in place thereof, so that the vertebra connecting portions 11 of the vertebral connecting plate 10 are superimposed on the upper and lower vertebra members 31 on the opposite sides of the artificial bone 30. In this state, the vertebra connecting portions 11 of the vertebral fusion plate 10 are slightly struck to thrust the projections 13 into the upper and lower vertebra members 31, so that the vertebral connecting plate 10 can be provisionally connected to the vertebral bodies 31. Thereafter, the set screws 20 are inserted in the threaded holes 14 and 15 and fastened by a hexagon wrench (not shown) which is successively fitted in the hexagonal recesses 23 of the threaded heads 21 of the vertebra connecting portions 11. Consequently, the thrusting threaded portions 22 of the set screws 20 are thrust in the vertebra members 31, so that the male threads of the threaded heads 21 are screwed in the threaded holes (female threads) 14 and 15 of the vertebral connecting plate 20. Since the displacement of the thrusting threaded portion 22 for a unit angular displacement of the set screw 20 is larger than that of the threaded head 21 due to a difference in pitch therebetween, a further rotation of the set screws 20 causes the vertebral connecting plate 10 to be firmly and rigidly connected to the vertebra members 31.

Consequently, the implanted bone 30 is firmly and rigidly connected to the upper and lower vertebra members 31 because the vertebral connecting plate 10 is connected to the vertebra members 31.

The inclination of the threaded holes 14 and 15 prevents the set screws 20 from being close to the spinal cord 32 and the nerve fascicle located in the vertebra members 31. The inclination angle of the threaded holes 14 and 15 depends on factors, such as the shapes of the vertebral connecting plate 10 and the vertebra connecting portions 11 thereof and/or the positions of the threaded holes 14 and 15, etc.

The connection of the vertebral connecting plate 10 to the vertebra members can be easily and quickly effected by the rotation of the set screws 20 with the help of the hexagon wrench which is fitted in the hexagonal recesses 23 of the threaded heads 21 of the set screws 20, thus resulting in an increased operating efficiency. The vertebral connecting plate 10 which is generally in the form of a flat plate has a cross sectional shape and thickness strong enough to resist a deformation, such as by torsion. Namely, no torsional deformation of the vertebral connecting plate 10 occurs in use.

FIG. 4 is a plan view of a vertebral connecting plate 10 according to another embodiment of the present invention. The connecting plate 40 is provided on its opposite ends with vertebra connecting portions 41 which have rounded corners and which are connected to each other through an intermediate connecting portion 41a which has a same width as the vertebra connecting portions 41.

Each of the vertebra connecting portions 41 has a pair of threaded holes 44 and 45 which are substantially diagonally spaced from and opposed to each other. Other features of this embodiment, not specifically mentioned above, are the same as the embodiment shown in FIG. 1A.

As can be seen from the above discussion, according to the present invention, a vertebral connecting plate having vertebra connecting portions at the opposite ends thereof and set screws which are screw-engaged in the associated threaded holes which are formed in the vertebra connecting portions. Each of the set screw has an engaging screw portion (threaded head) which is engaged in the associated threaded holes of the vertebral connecting plate and a thrusting screw portion (thrusting threaded portion) which is screwed in the vertebral members or bodies to be interconnected, which has a different pitch from that of the engaging screw portion, and which can also have a trapezoidal thread or a rectangular thread. Due to the difference in pitch, the vertebral connecting plate can be rigidly connected to the vertebra members. Furthermore, since the connecting operation of the vertebral connecting plate to the vertebral members or bodies can be easily effected simply by the rotation of the set screws about the center axis thereof, the surgical operation can be simplified.

We claim:

1. A vertebral connecting plate assembly comprising:
   a vertebral connecting plate which is provided, on its opposite ends, with vertebra connecting portions adapted to be connected to associated vertebra members, said vertebra connecting portions having threaded holes said threaded holes in each of said vertebra connecting portions being aligned along a line that intersects a longitudinal axis of said vertebral connecting plate at an oblique angle; and
   set screws having engaging screw portions which are engaged in said associated threaded holes of said vertebral connecting plate and thrusting screw portions which are adapted to be thrust in the vertebra members, said thrusting screw portions having a pitch larger than the pitch of said engaging screw portions.

2. The vertebral connecting plate assembly according to claim 1, wherein said threaded holes of said vertebra connecting portions are inclined with respect to a direction perpendicular to a plane of said vertebral connecting plate to prevent said set screws, when thrust into the vertebra members, from being close to nerve fascicle in the vertebra members.

3. The vertebral connecting plate assembly according to claim 2, wherein said vertebral connecting plate comprises an intermediate connecting portion which connects said vertebra connecting portions.

4. The vertebral connecting plate assembly according to claim 3, wherein said intermediate connecting portion has a width narrower than said vertebra connecting portions.

5. The vertebral connecting plate assembly according to claim 4, wherein said vertebra connecting portions have a thickness larger than that of said intermediate connecting portion.

6. The vertebral connecting plate assembly according to claim 5, wherein said vertebral connecting plate comprises projections with sharp apexes, provided on said vertebra connecting portions adapted to be thrust into the vertebra members.

7. The vertebral connecting plate assembly according to claim 3, wherein said intermediate connecting portion is said same width as the vertebra connecting portions.

8. The vertebral connecting plate assembly according to claim 7, wherein said vertebra connecting portions have a thickness larger than that of said intermediate connecting portion.

9. The vertebral connecting plate assembly according to claim 8, wherein said vertebral connecting plate comprises projections with sharp apexes, provided on the vertebra connecting portions adapted to be thrust into the vertebra members.

10. The vertebral connecting plate assembly according to claim 1, wherein said vertebra connecting portions are generally in the shape of a rectangle in plan view.

11. The vertebral connecting plate assembly according to claim 10, wherein each said vertebra connecting portion has a pair of threaded holes which are spaced from one another along a diagonal of the rectangle.

12. The vertebral connecting plate assembly according to claim 11, wherein said a pair of threaded holes of each said vertebra connecting portion are inclined in different directions with respect to a direction perpendicular to a plane of said vertebral connecting plate.

13. The vertebral connecting plate assembly according to claim 1, wherein each said vertebra connecting portion has a plurality of threded holes.

14. The vertebral connecting plate assembly according to claim 13, wherein said threaded holes of each said vertebra connecting portion are inclined in different directions with respect to a direction perpendicular to a plane of said vertebral connecting plate.

15. The vertebral connecting plate assembly according to claim 1, wherein said engaging screw portions of said set screws have a fine thread pitch, and said thrusting screw portions have a trapezoidal thread.

16. The vertebral connecting plate assembly according to claim 1, wherein said engaging screw portions of said set screws have a fine thread pitch, and said thrusting screw portions, have a rectangular thread.

17. The vertebral connecting plate assembly according to claim 1, wherein said vertebral connecting plate is coated with a biocompatible material.

18. A vertebral connecting plate comprising vertebra connecting portions adapted to be connected to associated vertebra members, and an intermediate connecting portion connecting said vertebra connecting portions, said vertebra connecting portions having threaded holes in which associated set screws are adapted to be screwed, said threaded holes in each of said vertebra connecting portions being aligned along a line that intersects the longitudinal axis of said vertebral connecting plate at an oblique angle.

19. The vertebral connecting plate according to claim 18, wherein said intermediate connecting portion has a width narrower than width of said vertebra connecting portions.

20. The vertebral connecting plate according to claim 19, wherein said vertebra connecting portions have a thickness larger than that of said intermediate connecting portion.

21. The vertebral connecting plate according to claim 20, wherein said vertebral connecting plate comprises projections with sharp apexes, provided on said vertebra connecting portions and adapted to be thrust into vertebral members to be connected.

22. A vertebral connecting plate comprises vertebra connecting portions adapted to be connected to associated vertebra members, and a solid and continuous central portion connecting said vertebra connecting portions, said vertebra connecting portions having threaded holes in which associated set screws are adapted to be screwed, said threaded holes of each of said vertebra connecting portions being aligned along an axis that is transverse to the longitudinal axis of said vertebral connecting plate.

* * * * *

UNITED STATES PATENT AND TRADEMARK OFFICE
CERTIFICATE OF CORRECTION

PATENT NO. : 5,147,361
DATED : September 15, 1992
INVENTOR(S) : Satoshi OJIMA et al.

It is certified that error appears in the above-indentified patent and that said Letters Patent is hereby corrected as shown below:

On the cover, in section [56], References Cited, line 3, change "Markoff" should be ---Markolf---.

On the cover, in section [57], Abstract, line 8, change "portion" to ---portions---.

At column 4, line 53 (claim 1, line 6) after "holes" (first occurrence) insert ---,---.

At column 5, line 23 (claim 7, line 3) change "said" to ---the---.

At column 5, line 23 (claim 7, line 3) change "the" to ---said---.

At column 5, line 50 (claim 13, line 3) change "threded" to ---threaded---.

At column 6, line 29 (claim 19, line 3) after "than" insert ---the---.

At column 6, line 39 (claim 21, line 5) change "vertebral" to ---vertebra---.

At column 6, line 40 (claim 22, line 1) change "comprises" to ---comprising---.

Signed and Sealed this

Third Day of October, 1995

*Attest:*

BRUCE LEHMAN

*Attesting Officer*    *Commissioner of Patents and Trademarks*